United States Patent
Janssen et al.

(10) Patent No.: US 9,671,370 B2
(45) Date of Patent: Jun. 6, 2017

(54) SYSTEM AND METHOD FOR DETECTING MATERIAL LOSS IN A TUBULAR

(71) Applicant: National Oilwell Varco, L.P., Houston, TX (US)

(72) Inventors: Matthias Janssen, Grossmoor (DE); Stefan Haberla, Celle (DE)

(73) Assignee: NATIONAL OILWELL VARCO, L.P., Houston, TX (US)

( * ) Notice: Subject to any disclaimer, the term of this patent is extended or adjusted under 35 U.S.C. 154(b) by 48 days.

(21) Appl. No.: 14/882,969

(22) Filed: Oct. 14, 2015

(65) Prior Publication Data

US 2017/0108468 A1  Apr. 20, 2017

(51) Int. Cl.
*G01N 27/82* (2006.01)
*E21B 47/00* (2012.01)
*G01N 27/72* (2006.01)

(52) U.S. Cl.
CPC .............. *G01N 27/82* (2013.01); *E21B 47/00* (2013.01); *G01N 27/72* (2013.01)

(58) Field of Classification Search
CPC ................... G01N 27/82; G01N 27/72; G01N 2291/2636; G01N 27/9046; E21B 47/0905; E21B 47/082
USPC ................................. 324/219–221, 240–243
See application file for complete search history.

(56) References Cited

U.S. PATENT DOCUMENTS

| | | | |
|---|---|---|---|
| 2,866,155 A | 12/1958 | Martin | |
| 4,710,712 A * | 12/1987 | Bradfield | G01N 27/9026 324/227 |
| 5,293,117 A * | 3/1994 | Hwang | G01N 27/82 324/220 |
| 5,914,596 A | 6/1999 | Weinbaum | |
| 2004/0016139 A1 | 1/2004 | Lam et al. | |
| 2004/0100256 A1* | 5/2004 | Fickert | E21B 47/082 324/221 |
| 2006/0096753 A1 | 5/2006 | Zheng et al. | |
| 2010/0148766 A1* | 6/2010 | Weischedel | G01N 27/9033 324/238 |

(Continued)

OTHER PUBLICATIONS

International Patent Application No. PCT/US2016/056605 International Search Report and Written Opinion dated Dec. 23, 2016 (14 pages).

(Continued)

*Primary Examiner* — Jay Patidar
(74) *Attorney, Agent, or Firm* — Conley Rose, P.C.

(57) ABSTRACT

A method and system for detecting material loss in a tubular. A method includes identifying a radial cross-sectional area of a tubular as having a loss of material in a wall of the tubular. Responsive to the identifying, an amount of voltage offset present in each of a plurality of measurement signals is determined. Each of the measurement signals provides measurement information for an arc section of the wall. For each of the measurement signals, a zero adjusted signal is produced by adjusting the measurement signal to remove the amount of voltage offset over a length of the tubular for which the identifying recognizes the loss of material. An assessment of wall material loss is produced for each arc section of the wall of the tubular based on the zero adjusted signals. An image of the wall of the tubular showing the wall material loss for each arc section is generated.

21 Claims, 8 Drawing Sheets

(56) References Cited

U.S. PATENT DOCUMENTS

2012/0109565 A1* 5/2012 Tsukada ................ G01N 27/83
  702/106

OTHER PUBLICATIONS

Stanley, Roderic K. et al., "Results From NDE Inspections Of Coiled Tubing," Society of Petroleum Engineers, SPE 46023, 1998, pp. 91-103.

* cited by examiner

SYSTEM AND METHOD FOR DETECTING MATERIAL LOSS IN A TUBULAR

BACKGROUND

Continuous tubular strings formed of connectable tubular sections or elements, such as production tubing strings, strings of drill pipe and casing strings, are used in the drilling, completion and production of subterranean oil and gas wells. The tubular elements comprising such strings are subject to mechanical damage while the tubular elements are located within the well and are also subject to the action of corrosive fluids which may be contained within the tubular elements or which may be transported through the tubular string between the well surface and a downhole location. It is therefore advantageous that the individual tubular elements of a tubular string be inspected periodically. Commonly, tubular elements or tubular sections are inspected for defects after the tubing string is removed from the well. Conventional inspection of tubular sections normally occurs after the individual tubing sections comprising the tubing string have been disengaged. Defect inspections are conventionally performed on a section by section basis. Occasionally, inspection is performed downhole through the use of inspection calipers.

SUMMARY

A system and method for detecting loss of material in a tubular are disclosed herein. In one embodiment, a method for detecting loss of material in a tubular includes identifying a radial cross-sectional area of a tubular as having a loss of material in a wall of the tubular. Responsive to the identifying, an amount of voltage offset present in each of a plurality of measurement signals is determined. Each of the measurement signals provides measurement information for an arc section of the wall. For each of the measurement signals, a zero adjusted signal is produced by adjusting the measurement signal to remove the amount of voltage offset over a length of the tubular for which the identifying recognizes the loss of material. An assessment of wall material loss is produced for each arc section of the wall of the tubular based on the zero adjusted signals. An image of the wall of the tubular showing the wall material loss for each arc section is generated.

In another embodiment, a system for detecting material loss in a tubular includes a magnetization coil, a measurement coil, a plurality of flux leakage sensors, and a processor. The magnetization coil is configured to encircle the tubular and generate a magnetic field that induces magnetic flux in the tubular. The measurement coil is configured to encircle the tubular and detect changes in the magnetic flux caused by variation in the radial cross-section of the tubular. The plurality of flux leakage sensors are arranged to radially encircle the tubular. Each of the flux leakage sensors is configured to detect changes in the magnetic field of an arc section of the tubular. The processor is coupled to the measurement coil and the flux leakage sensors. The processor is configured to identify a radial cross-sectional area of the tubular as having a loss of material in a wall of the tubular based on a flux signal generated by the measurement coil, and responsive to identification of the loss of material, to determine an amount of voltage offset present in each measurement signal generated by the flux leakage sensors. The processor is also configured, for each measurement signal, to produce a zero adjusted signal by adjusting the measurement signal to remove the amount of voltage offset over a length of the tubular for which the loss of material is detected, to produce an assessment of wall material loss for each arc section of the wall of the tubular based on the zero adjusted signals; and to generate an image of the wall of the tubular showing the wall material loss for each arc section.

In a further embodiment, a non-transitory computer-readable medium is encoded with instructions that when executed cause a processor to identify a radial cross-sectional area of the tubular as having a loss of material in a wall of the tubular, and responsive to identification of loss of wall material in a radial cross-sectional area, to determine an amount of voltage offset present in each of a plurality of measurement signals. Each of the measurement signals provides measurement information for an arc section of the wall of the tubular. The instructions also cause the processor to produce, from each of the measurement signals, a zero adjusted signal by adjusting the measurement signal to remove the amount of voltage offset over a length of the tubular for which the loss of material is detected, to produce an assessment of wall material loss for each arc section of the wall of the tubular based on the zero adjusted signals, and to generate an image of the wall of the tubular showing the wall material loss for each arc section.

BRIEF DESCRIPTION OF THE DRAWINGS

For a detailed description of exemplary embodiments of the invention, reference will now be made to the figures of the accompanying drawings. The figures are not necessarily to scale, and certain features and certain views of the figures may be shown exaggerated in scale or in schematic form, and some details of conventional elements may not be shown in the interest of clarity and conciseness.

NOTATION AND NOMENCLATURE

Certain terms are used throughout the following description and claims to refer to particular system components. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through direct engagement of the devices or through an indirect connection via other devices and connections. The recitation "based on" is intended to mean "based at least in part on." Therefore, if X is based on Y, X may be based on Y and any number of other factors.

DETAILED DESCRIPTION

In the drawings and description that follow, like parts are typically marked throughout the specification and drawings with the same reference numerals. The present disclosure is susceptible to embodiments of different forms. Specific embodiments are described in detail and are shown in the drawings, with the understanding that the present disclosure is to be considered an exemplification of the principles of the disclosure, and is not intended to limit the disclosure to that illustrated and described herein. It is to be fully recognized that the different teachings and components of the embodiments discussed below may be employed separately or in any suitable combination to produce desired results.

Various conventional techniques are available for identifying defects in tubulars such as drill pipes, production tubing, casing, etc. Unfortunately, conventional techniques as subject to a number of limitations and disadvantages. For example, techniques that employ surface-riding detectors, require insertion of a detector or a driving means within the bore of tubular elements, or require rotating mechanical means to obtain a complete circumferential coverage of tubing sections are unsuited for use in defect inspection and measurement of tubing sections while a tubing string is being removed from a well. Such defect inspection techniques are also unsuited to the measurement of defects in tubing sections while the sections are interconnected in the tubing string. Thus these inspection techniques are not suitable for use on a drilling, completion, or workover rig at the surface of the well to measure defects in a tubing string as the string is removed from the well. Techniques that employ radioactive sources are also problematic, and present additional issues, such as the need to comply with burdensome regulatory requirements.

The system and method disclosed herein employ magnetic flux measurements to detect material loss in a tubular without requiring insertion into the bore of the tubular. Accordingly, embodiments can be employed to inspect and determine the condition of strings of tubulars being removed from a borehole. Embodiments employ a first magnetic inspection technique to identify a cross-section of a tubular that is subject to material loss, and employ a second magnetic detection technique to identify an arc section of the tubular from which material has been lost. The identification of the cross-section triggers run-time calibration of the second technique without which the second technique would be unusable. Embodiments further process signals resulting from application of the second technique to mitigate overemphasis present at the beginning and end of an area of material loss.

Figure 1:
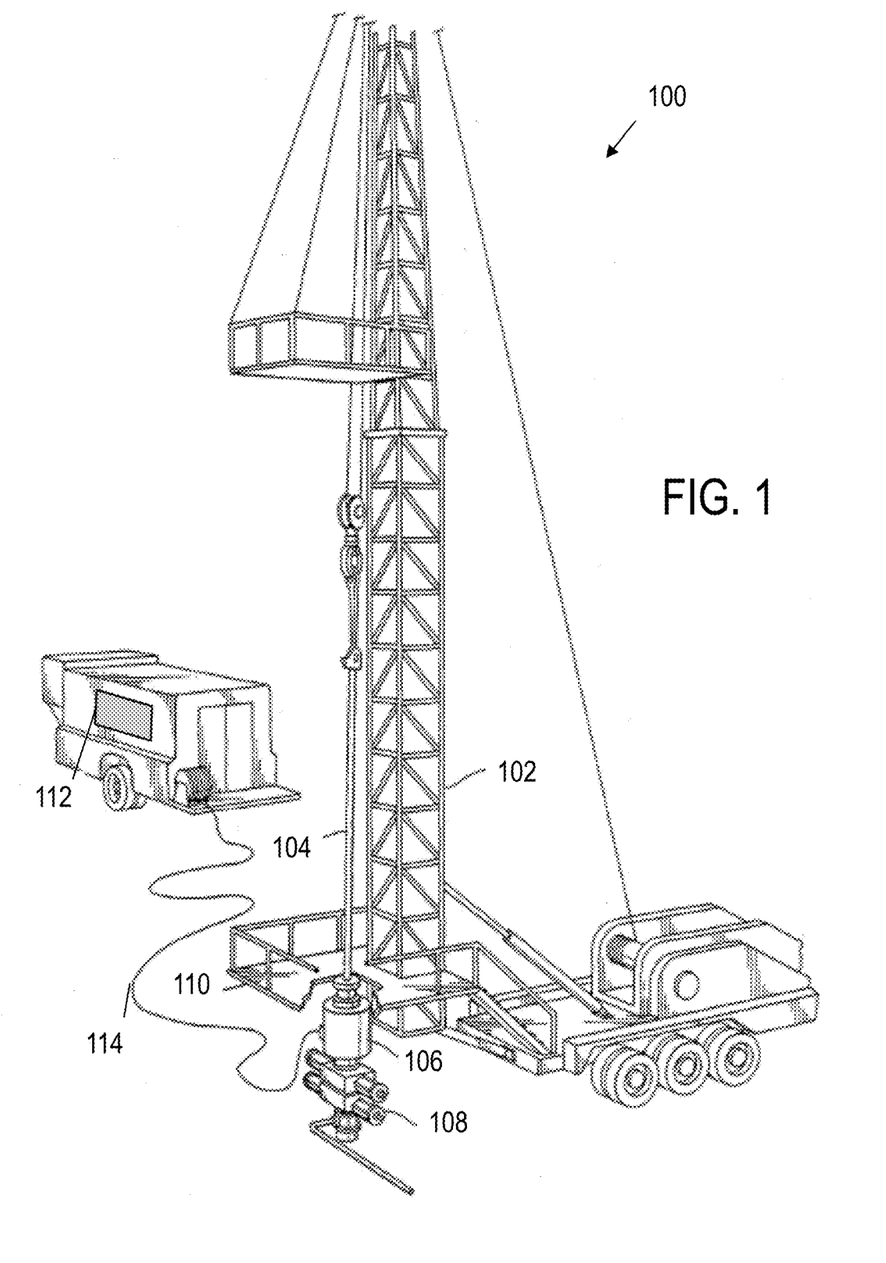
FIG. 1 shows a well environment that includes a system for detecting material loss in a tubular in accordance with principles disclosed herein.

FIG. 1 shows a well environment 100 that includes a system for detecting material loss in a tubular in accordance with principles disclosed herein. The environment 100 includes a workover rig 102 that is used to remove a tubular string 104 from an oil or gas well during workover operations. The tubing string 104 may include casing, drill pipe, production tubing, or other tubulars used downhole. Workover operations may involve the removal of the tubing string 104 from the well to permit operations intended to restore or increase production in a producing well. Typically, the original tubing string 104 is reused if the respective tubular elements are in satisfactory condition. The environment 100 also includes a tubing inspection tool 106 at the rig site to measure defects in each tubular element as it is removed from the well. The tubing inspection tool 106 can be positioned on the wellhead 108 below the rig floor 110 so as not to interfere with conventional operations on the rig. The tubing inspection tool 106 can be attached directly to the blowout preventers on the well.

The tubing inspection tool 106 generates signals that are representative of the state or condition of the wall of the portion of the tubing string 104 passing through the tubing inspection tool 106. For example, the signals generated by the tubing inspection tool 106 may indicate whether material of the wall of the portion of the tubing string 104 passing through the tubing inspection tool 106 has been lost. The tubing inspection tool 106 is coupled to a tubing inspection processor 112 via a communication medium 114. The signals generated by the tubing inspection tool 104 are transmitted to the tubing inspection processor 112 via the communication medium 114. The communication medium 114 may be a cable that includes optically or electrically conductive elements. In some embodiments, the communication medium 114 may include a wireless channel that may be used to transfer measurements from the tubing inspection tool 106 to the tubing inspection processor 112. In some embodiments, the tubing inspection processor 112 may be located on-site, as illustrated in FIG. 1. In other embodiments, the tubing inspection processor 112 may be located at a remote site (e.g., in a different country from the tubing inspection tool 106), and the communication medium 114 may include wired or wireless networks (e.g., satellite links, the Internet, etc.) through which the signals generated by the tubing inspection tool 106 are transferred to the tubing inspection processor 112.

The tubing inspection processor 112, receives the signals generated by the tubing inspection tool 106, and processes the signals to identify a loss of wall material in the tubing string 104. The tubing inspection processor 112 applies the signals generated by a first measurement instrument of the tubing inspection tool 106 to trigger run-time calibration of the signals generated by a second measurement instrument of the tubing inspection tool 106. The calibration allows the signals generated by the second measurement instrument to be used to isolate wall material loss to an arc segment of the tubular wall. Without this calibration the signals generated by the second measurement instrument would not be usable to determine the location of the material loss. For example, without this calibration, the tubing inspection processor 112 would be unable to determine, based on the signals generated by the second measurement instrument, whether material loss in a cross-section of a tubular is concentrated in a particular radial segment of the tubular or distributed evenly over the entire wall area of the cross-section.

Figure 2:
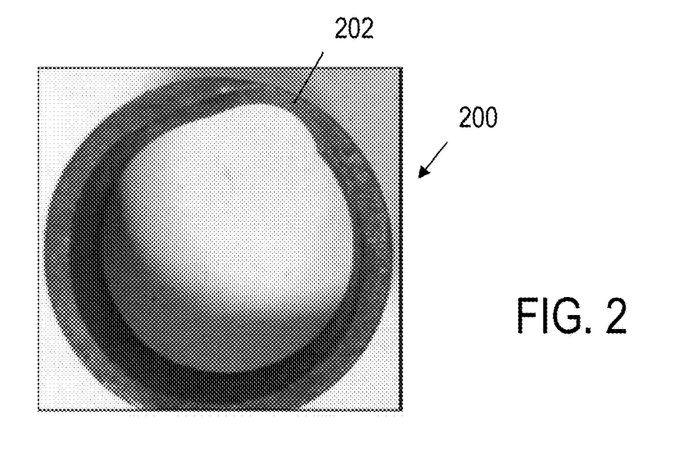
FIG. 2 shows an end view of a tubular exhibiting material loss due to scraping of a sucker rod on the interior wall of the tubular.

FIG. 2 shows an end view of an illustrative tubular 200 that has loss of wall material in an isolated area 202. Material loss in the isolated area 202 of the wall of the tubular 200 may be caused by, for example, scraping of a sucker rod against the internal surface of the tubular 200. A sucker rod is a steel rod disposed in the bore of the tubular 200 that connects the surface and downhole components of a reciprocating pump installed on a well. The sucker rod tends to rub a same area of the internal wall of the tubular 200, and over time to cause the loss of material shown in FIG. 2. An isolated loss of material weakens the tubular to a significantly greater degree than if the material loss were evenly distributed over the cross-section of the tubular. Accordingly, the tubing inspection processor 112 applies the signals generated by the first and second measurement instruments of the tubing inspection tool 106 to identify an area of the tubing wall where material has been lost. The material loss illustrated in FIG. 2 may be present at any longitudinal location of the tubular 200. Accordingly, FIG. 2 represents an end view of the tubular 200 taken from any cross section along the length of the tubular 200.

Figure 3:
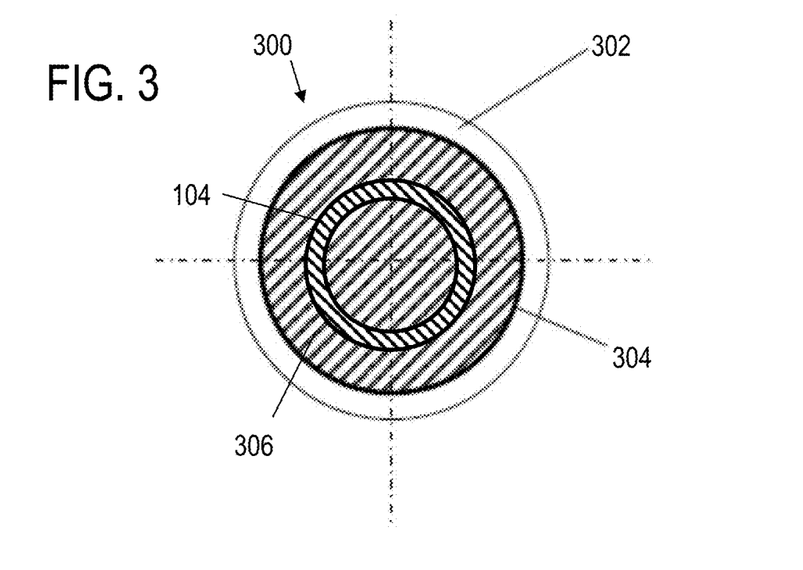
FIG. 3 shows a schematic diagram of a tool for detecting material loss in a cross-section of a tubular in accordance with principles disclosed herein.

FIG. 3 shows a schematic diagram for a first measurement instrument 300 included in the tubing inspection tool 106. The first measurement instrument may also be referred to as a cross-sectional area tool 300. The cross-sectional area tool 300 includes a magnetization coil 302 and a measurement coil 304. The tubing string 104 passes through the bore 306 of the cross-sectional area tool 300. Direct current flow in the magnetization coil 302 produces a saturating magnetic field in the bore 306. The measurement coil 304 measures the magnetic flux induced in the tubing string 306 by the magnetic field. The tubing string 104 within the saturating magnetic field is saturated when the magnitude of the magnetic field induced in the tubing string 104 is at a maximum and does not increase as a result of a further increase in the saturating magnetizing field. Thus, the saturating magnetizing field can produce a uniform saturated magnetic field in a tubing section having a given cross-sectional area. In other words, the total magnetic flux is dependent upon the cross-sectional area or wall thickness of the tubing string 104. If the saturating magnetizing field is uniform, the contribution of the total flux induced by the magnetization of the tubing material within a given area varies in accordance with the cross-sectional area of the tubing section. Thus, the magnetic flux changes as the cross-sectional area of the tubing string 104 within the bore 306 changes. The signal generated by the measurement coil 302 and transmitted to the tubing inspection processor 112 is representative of the magnetic flux, and correspondingly representative of the cross-sectional area of the portion of the tubing string 104 within the bore 306. However, the signal generated by the cross-sectional area tool 300 is indicative only of the total cross-sectional area of the tubing section 104 and provides no information with regard whether material loss is uniform over the cross-section or isolated to a particular arc portion of the cross-section.

Figure 4:
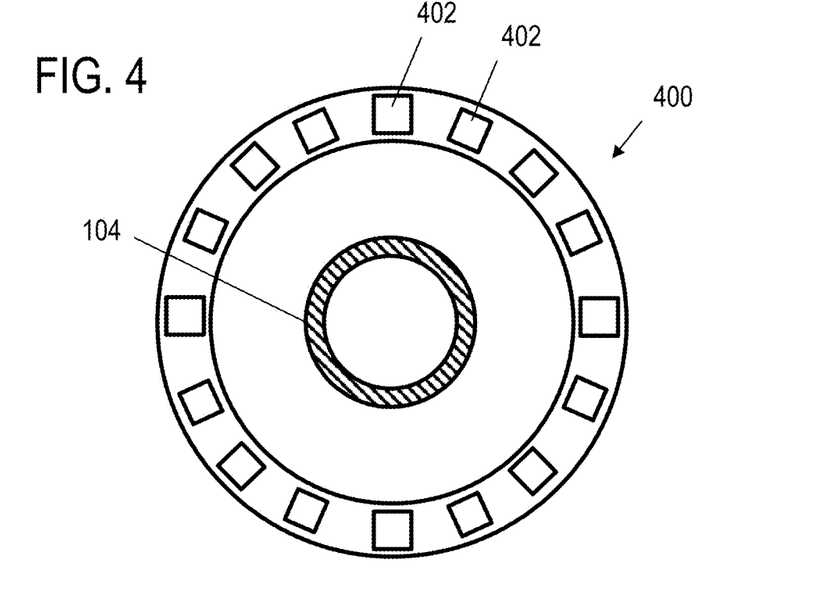
FIG. 4 shows a schematic diagram for a tool for isolating material loss to an arc section of a tubular in accordance with principles disclosed herein.

FIG. 4 shows a schematic diagram for a second measurement instrument 400 included in the tubing inspection tool 106. The second measurement instrument 400 may also be referred to as a sectional wall tool 400. While the cross-sectional area tool 300 provides information related to the total cross-sectional area of the tubing string 104, the sectional wall tool 400 provides information related to the cross-sectional area of arc sections of the tubing string 104. The sectional wall tool 400 includes a plurality of flux leakage sensors 402 arranged as a ring. The sectional wall tool 400 may include any number of flux leakage sensors 402, and has been illustrated in FIG. 4 as including sixteen sensors 402 at 22.5° of angular offset as a matter of convenience. Other embodiments of the sectional wall tool 400 may include a different number of sensors 402 at a different angular offset.

The tubing string 104 pass through the interior of the ring and each of the flux leakage sensors 402 detects flux leakage in a portion (i.e., an arc section) of the tubing string 104 closest to the flux leakage sensor 402. In some embodiments, the flux leakage sensors 402 may include Hall sensors. The flux leakage detected by each of the sensors 402 is related to the area of the tubing wall string material nearest the sensor 402. Accordingly, the signals generated by the sectional wall tool 400 provide information indicative of the wall thickness or material loss of the tubing string 104 at a number of angular positions, thereby potentially allowing the tubing inspection processor 112 to identify areas of isolated material loss in the tubing string 104.

Figure 5A:
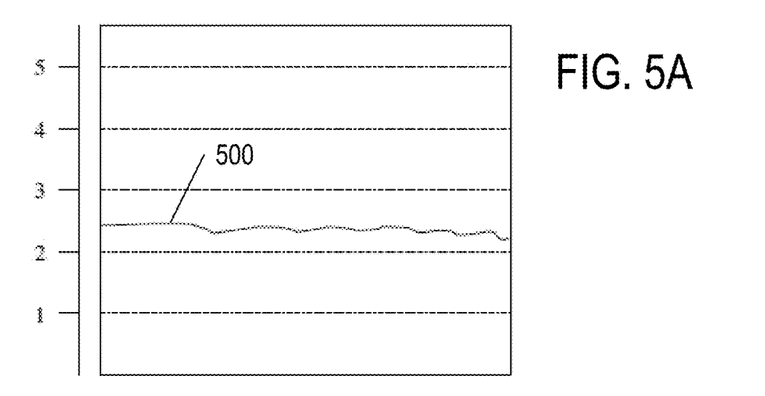
FIGS. 5A-5C show zero adjustment and amplification of signals in accordance with principles disclosed herein.
Figure 5B:
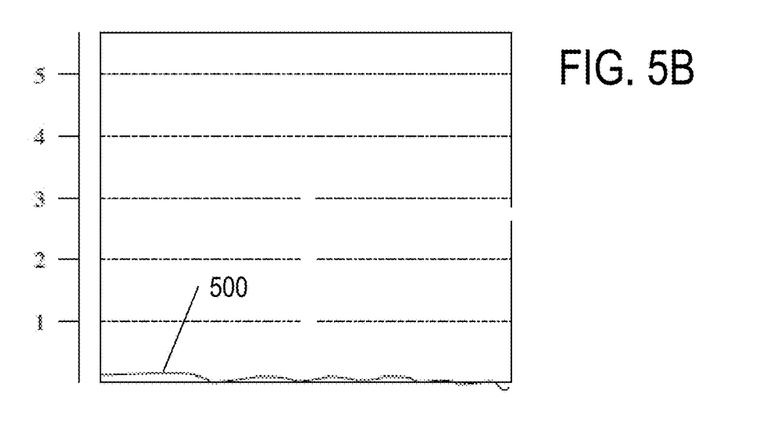
Figure 5C:
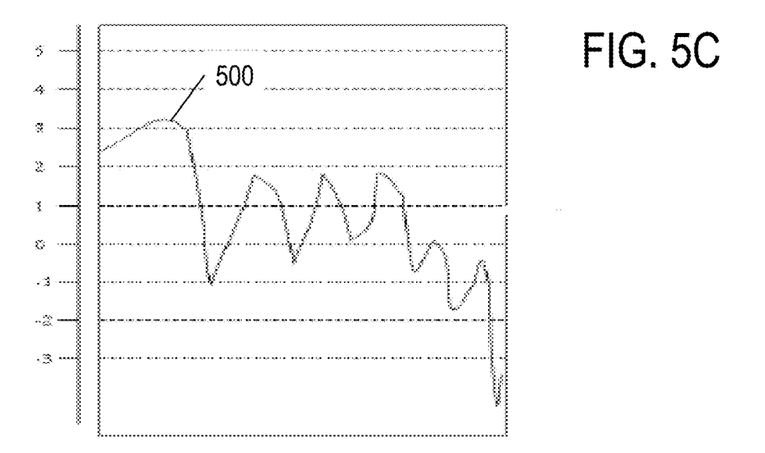

The signal voltages generated by the sensors 402 are very small, and substantial gain must be applied to the signals. The signals generated by the sensors 402 include a DC component, also referred to herein as a voltage offset or a DC (direct current) offset. In order to amplify the signals generated by the sensors 402, the DC component must be removed from the signals. Removal of the DC component from a signal output of a sensor 402 may be referred to as "zero adjustment." FIGS. 5A-5C show examples of an output signal of one of the sensors 402. In FIG. 5A, the output signal 500 includes a large DC offset relative to the AC amplitude of the signal 500. In FIG. 5B, the signal 500 has been zero adjusted to eliminate the DC offset. In FIG. 5C, gain has been applied to the zero-adjusted signal.

Figure 6:
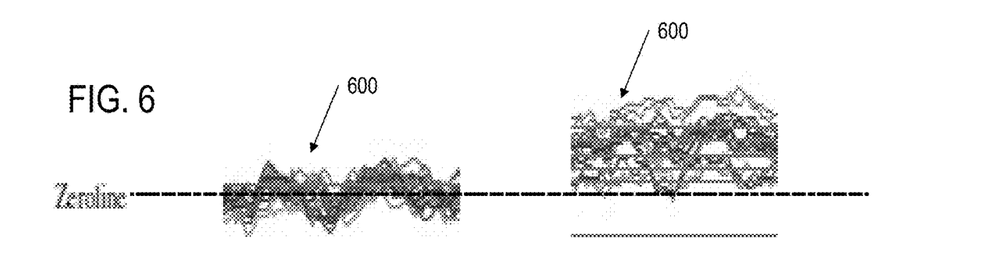
FIG. 6 shows spreading of measurement signals with time.

Over time, the DC offset present in the output signal of each of the sensors 402 drifts. FIG. 6 shows output signals 600 of the sensors 402 about a zeroline after zero adjustment, and shows each of the signals 600 with a different amount of DC offset after a period of operation subsequent to zero adjustment. The DC drift may be caused by mechanical effects, such as movement of the tubing string 104 through the tubing inspection tool 104 or movement of the sensors 402. The accumulated DC offset renders the signals 600 unusable.

Figure 7:
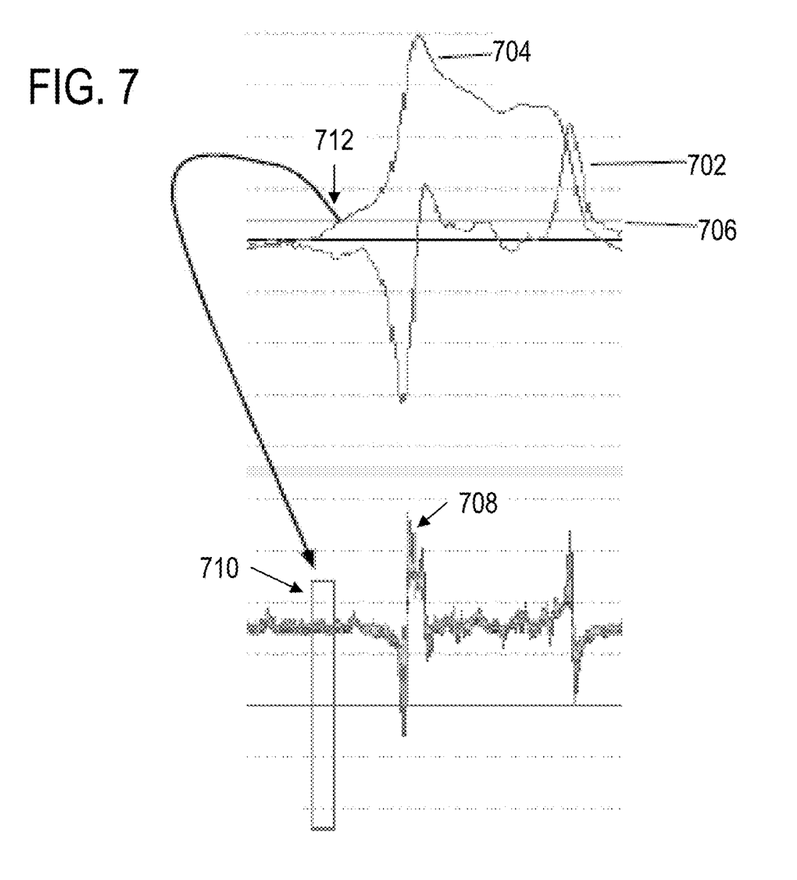
FIG. 7 shows thresholding of cross-sectional area signal in accordance with principles disclosed herein.

FIG. 7 shows signals generated by the tubing inspection tool 104 and the tubing inspection processor 112 as the tubing string 104 moves through the tubing inspection tool 106. The signal 702 is the raw output of the cross-sectional area tool 300. The signals 708 are the outputs of the sectional wall tool 400. The signal 704 is an integrated version of the signal 702 which may be numerically generated by the tubing inspection processor 112 or generated by a filter in the inspection processor 112 or the tubing inspection tool 106. The integration aids in transient suppression. The tubing inspection processor 112 generates a threshold value 706 that the tubing inspection processor 112 compares to the integrated output of the cross-sectional area tool 300. When the tubing inspection processor 112 detects that the integrated output of the cross-sectional area tool 300 exceeds the threshold 706, as shown at time 712, the tubing inspection processor 112 deems the cross-sectional area of the tubing string 104 to have lost wall material.

To apply the output signals 708 of the sectional wall tool 400 to identify an arc section of the tubing wall from which the material has been lost, the tubing inspection processor 112 determines a zero adjustment value for each of the signals 708. That is, for each output signal of a sensor 402, the tubing inspection processor 112 determines a zero adjustment value to eliminate DC offset from the output signal. The zero adjustment value for each sensor 402 may be different. For each sensor 402, the tubing inspection processor 112 generates the zero adjustment value for a signal by retrieving one or more samples of the signal generated by the sensor 402 that were produced prior to the time of wall loss detection (i.e., prior to time 712). In FIG. 7, the sample values retrieved by the tubing inspection processor 112 to generate a zero adjustment value are illustrated as signal values 710. For example, the signal values 710 may be stored in memory of the tubing inspection processor 112, and the tubing inspection processor 112 can access the location in memory (e.g., at a known address offset that corresponds to the previous time) that contains the signal values 710 to retrieve the signal values 710.

In some embodiments, tubing inspection processor 112 may generate the zero adjustment value by retrieving a number of values of the signal 708 generated prior to the trigger event at time 712 and compute the average of the signal values. For example, the tubing inspection processor 112 may retrieve N consecutive signal values 710, sum the signal values 710, and divide the sum by N (e.g., N=4) to produce a zero adjustment value.

After determining a new zero adjustment value for each of the sensors 402, the tubing inspection processor 112 applies the zero adjustment value to the output of the corresponding sensor 402 to remove DC offset. The offset adjusted signal can be amplified as needed to facilitate further processing. A new zero adjustment value may be determined for each sensor 402 each time an area of material loss is identified.

Figure 8:
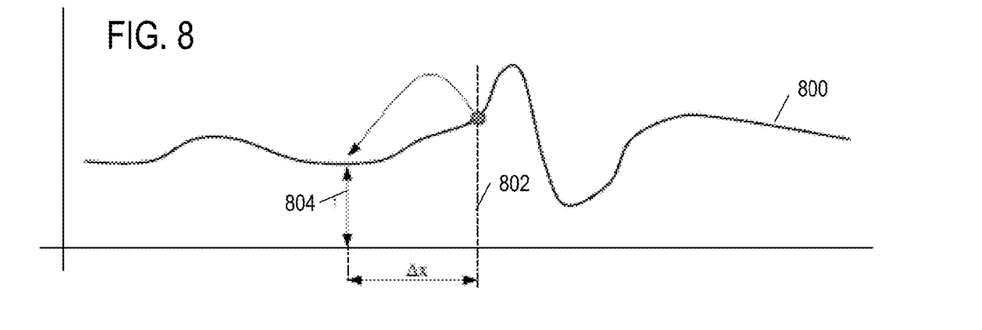
FIGS. 8 and 9 show selection of values of zero adjustment in accordance with principles disclosed herein.

FIGS. 8 and 9 shows additional examples of zero adjustment value selection by the tubing inspection processor 112. In FIG. 8, an output signal 800 of the sectional wall tool 400 is shown. At time 802, the tubing inspection processor 112 detects the integrated output of the cross-sectional area tool 300 exceeding the threshold 706. Responsive to the cross-sectional area tool output exceeding the threshold 706, the tubing inspection processor 112 retrieves a sample of the sectional wall tool output signal that was produced at time 804, Δx prior to time 802, for use in zero adjusting the signal 800.

Figure 9:
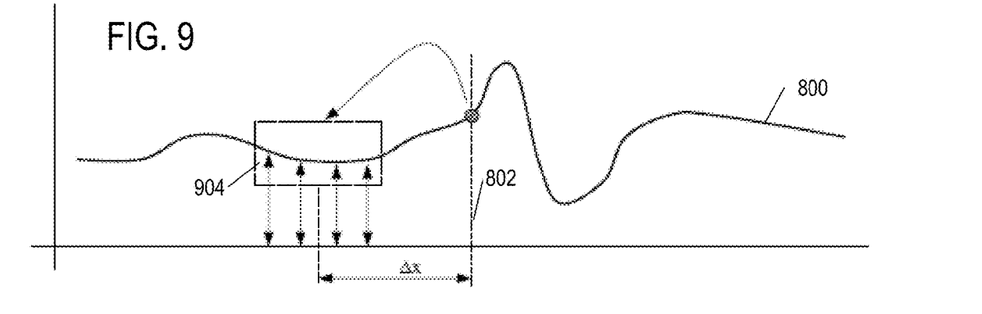

In FIG. 9, an output signal 800 of the sectional wall tool 400 is again shown, and at time 802, the tubing inspection processor 112 detects the integrated output of the cross-sectional area tool 300 exceeding the threshold 706. Responsive to the cross-sectional area tool output exceeding the threshold, the tubing inspection processor 112 retrieves multiple samples (N samples) of the sectional wall tool output signal produced during time interval 904 (i.e., occurring about Δx prior to time 802). The N samples may be summed and divided by N to generate an average sample value that can be used to zero adjust the signal 800.

Figure 10:
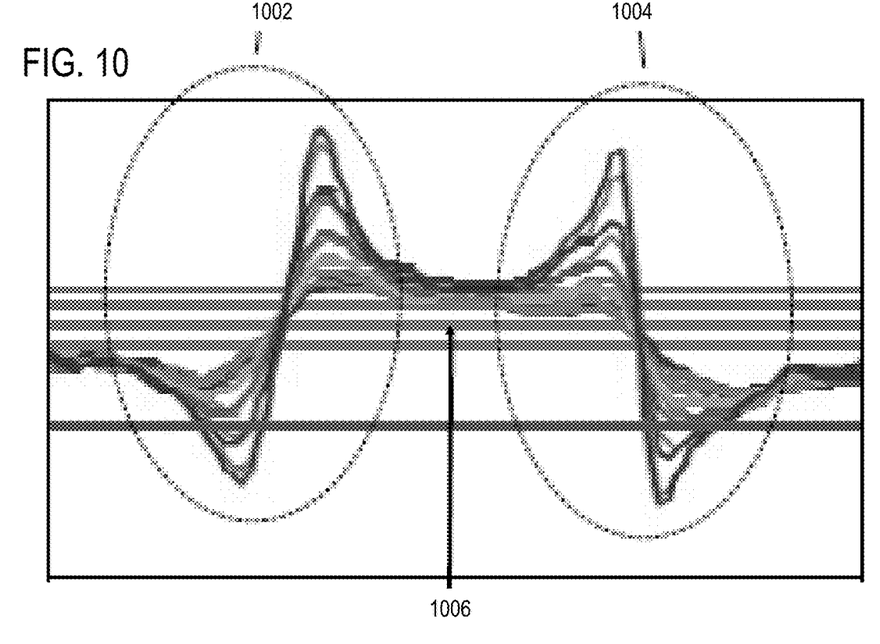
FIG. 10 shows overemphasis in sectional wall measurement signals at the beginning and end of an area of material loss.

As explained above, a zero adjustment value is computed for each output signal of a sensor 402 and the output signals of sectional wall tool 400 are zero adjusted using the zero adjustment values. The signals generated by the sensors 402 at the start and the end of an area of material loss tend to be overemphasized, while between the start and the end of an area of material loss the signals generated by the sensors 402 may be relatively small and weak. FIG. 10 shows an example of the signals output by the sectional wall tool 400 when a loss in wall material in the tube string 104 is encountered. Areas 1002 and 1004 are overemphasized, and correspond to the beginning and end of the area of material loss. Between areas 1002 and 1004, in area 1006, the signals are relatively weak and the differences between the signals are small. To compensate for the overemphasis, the tubing inspection processor 114 rectifies and standardizes the signals output by the sectional wall tool 400. After the signals generated by the sensors 402 have been zero adjusted, as described above, the tubing inspection processor 112 rectifies the zero adjusted signals. Rectification flips portions of the signal below the zero line, such that the flipped portions of the signal are above the zero line. The tubing inspection processor 112 may implement rectification by computing the absolute value of each sample of signal or by negating each negative sample value (e.g., multiplying negative samples by −1, inverting the sign bit of negative samples, etc.).

The tubing inspection processor 112 standardizes the rectified signals. Standardization scales tubular length correspondent sample values of the signals generated by the sensors 402 (i.e., the signals representing wall thickness or material loss in the arc sections of the tubular acquired at a same longitudinal position of the tubular) to produce standardized values that better reflect the proportionality of the sample values. In some embodiments, the tubing inspection processor 112 may implement standardization by, for each set of length correspondent samples, dividing each of the samples by the sum of the samples. For example, the sensors 402 may generate measurements of the tubular wall at intervals of 0.001 meters, and the measurement values produced by the sensors 402 at each 0.001 interval position forms a set of samples that are standardized as described herein.

Figure 11:
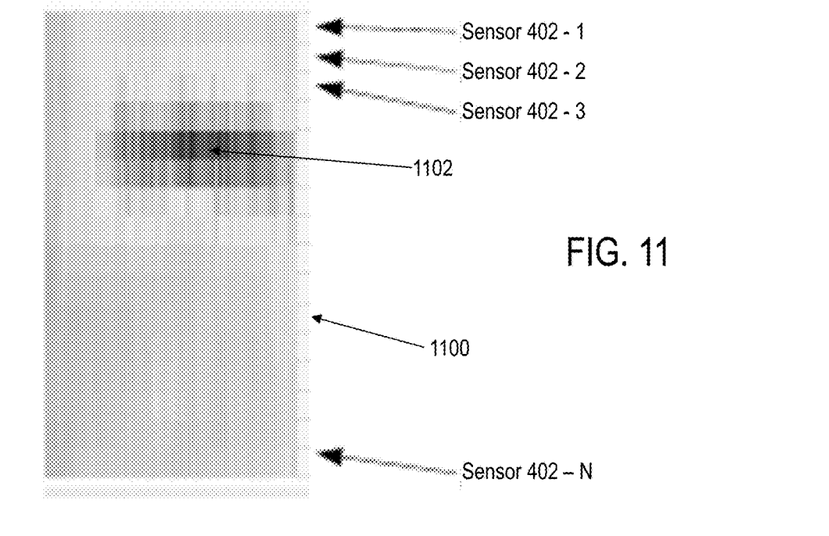
FIG. 11 shows a map of material loss in a tubular generated in accordance with principles disclosed herein.

The tubing inspection processor 112 generates map of the tubular showing the relative thickness of or material loss in the tubular wall in the arc sections corresponding to each of the sensors 402. Thus, the map shows areas of the tubular that have lost wall material. FIG. 11 shows an example of a map 1100 generated by the tubing inspection processor 112. The output measurements of each sensor 402 are shown, and color or shading is provided to illustrate the degree of wall loss. In FIG. 11, area 1102 shows the greatest degree of wall loss. Color or shading may be selected by the tubing inspection processor 112 base on threshold values that are compared to the standardized signal values.

Various operations may be performed based on the map 1100 or other notifications of material loss generated by the tubing inspection processor 112. For example, a length of the tubing section 104 having wall loss that exceeds a predetermined amount may be removed from the tubing string 104 and replaced with a different section of tubing.

Figure 12:
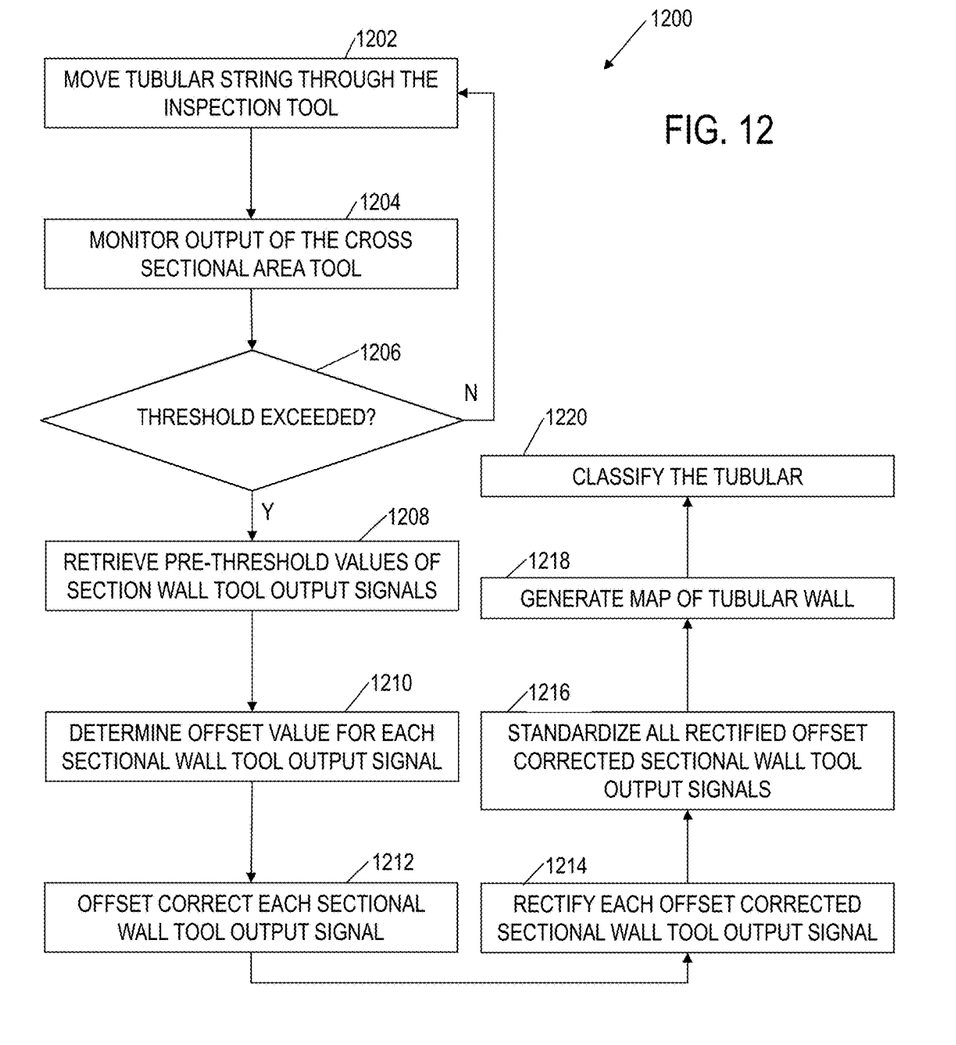
FIG. 12 shows a flow diagram for a method for detecting material loss in a tubular in accordance with principles disclosed herein.

FIG. 12 shows a flow diagram for a method 1200 for detecting material loss in a tubular in accordance with principles disclosed herein. Though depicted sequentially as a matter of convenience, at least some of the actions shown can be performed in a different order and/or performed in parallel. Additionally, some embodiments may perform only some of the actions shown. In some embodiments, at least some of the operations of the method 1200, as well as other operations described herein, can be implemented as instructions stored in a computer readable storage device and executed by a processor.

In block 1202, the tubing string 104 is moving through the tubing inspection tool 102. In some embodiments, the tubing inspection tool 102 may move along the tubing string 104. The cross-sectional area tool 300 is generating a magnetic field and measuring the magnetic flux induced in the tubing string 104 by the magnetic field. The sectional wall tool 400 is measuring flux leakage in a plurality of arc sections of the tubing string 104.

In block 1204, the tubing inspection processor 112 is receiving measurements from the tubing inspection tool 102. The measurements include measurement values produced by the cross-sectional area tool 300 and measurement values produced by the sectional wall tool 400. The tubing inspection processor 112 monitors the measurement values produced by the cross-sectional area tool 300 to determine whether the tubing string 104 has lost material in the cross-sectional area currently being magnetized. The tubing inspection processor 112 may integrate the signal received from the cross-sectional area tool 300 to suppress transients.

The tubing inspection processor 112 may also store the received measurements in memory for processing at a later time.

In block 1206, the tubing inspection processor 112 determines whether the signal received from the cross-sectional area tool 300 indicates that an area of material loss has been encountered. An area of material loss may be identified if the amplitude of signal received from cross-sectional area tool 300 crosses a predetermined threshold, where the threshold is set to recognize a predetermined amount of material loss in the cross-sectional area of the tubing string 104.

If measurements of the cross-sectional area of the tubing string 104 indicate that the tubing string 104 has lost material, then, in block 1208, for each measurement signal generated by the sectional wall tool 400, the tubing inspection processor 112 retrieves a stored value of the signal generated by the sectional wall tool 400 at a location of the tubing string 104 measured prior to the location at which the material loss is identified (i.e., the location at which the threshold is exceeded). In some embodiments, the tubing inspection processor 112 may retrieve multiple values of the signal generated by the sectional wall tool 400 at a location of the tubing string 104 measured prior to the location at which the material loss is identified.

In block 1210, the tubing inspection processor 112 determines an offset value for each measurement signal generated by the sectional wall tool 400. In some embodiments, a single value of measurement signal retrieved in block 1208 may serve as the offset value. In other embodiments, multiple retrieved values may be averaged, and the average value may serve as the offset value. A new/different offset value is determined for each measurement signal generated by the section wall tool 400 each time an area of cross-sectional material loss is identified using the signal generated by the cross-sectional area tool 300.

In block 1212, the tubing inspection processor 112 zero adjusts (i.e., offset corrects) each measurement signal generated by the sectional wall tool 400 by subtracting from the signal the offset value determined for the signal. In some embodiments, the tubing inspection processor 112 may retrieve multiple values of the signal generated by the sectional wall tool 400 at a location of the tubing string 104 measured prior to the location at which the material loss is identified, and average the values to produce a value of offset to be removed from the signal for zero adjustment.

In block 1214, the tubing inspection processor 112 rectifies the zero adjusted signals as explained above.

In block 1216, the tubing inspection processor 112 standardizes the rectified zero adjusted signals as explained above.

In block 1218, the tubing inspection processor 112 generates a map of the wall of the tubing string 104. The map shows relative wall thickness or material loss measured by each of the sensors 402 of the sectional wall tool 400. A change in wall thickness or material loss may be indicated by a change of shade or color, where the change is triggered by a signal value crossing a threshold associated with a shade or color.

In block 1220, the sections (i.e., tubulars) of the tubing string 104 are classified based on the nature of the material loss identified. For example, a section of the tubing string 104 having excessive material loss in an isolated area, as would be caused by scraping of a sucker rod, may be removed from the tubing string 104 and replaced by a different section of tubing. In other embodiments, sections of tubing exhibiting material loss may be categorized based on the degree and nature of material lost for use in applications in which the material loss is acceptable.

Figure 13:
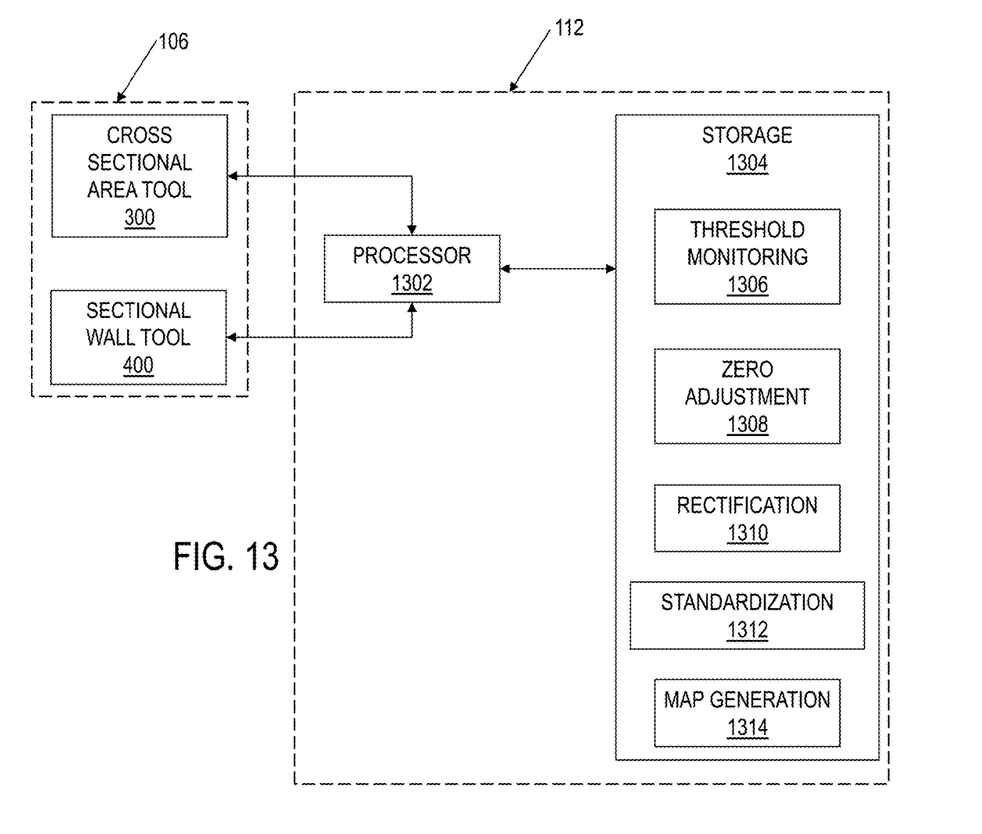
FIG. 13 shows a block diagram for a processing system for detecting material loss in a tubular in accordance with principles disclosed herein.

FIG. 13 shows a block diagram of the tubing inspection processor 112. The tubing inspection processor 112 includes a processor 1302 and storage 1304. The processor 1302 may be a general-purpose microprocessor, digital signal processor, microcontroller, or other device capable of executing instructions retrieved from a computer-readable storage medium. Processor architectures generally include execution units (e.g., fixed point, floating point, integer, etc.), storage (e.g., registers, memory, etc.), instruction decoding circuitry, peripherals (e.g., interrupt controllers, timers, direct memory access controllers, etc.), input/output systems (e.g., serial ports, parallel ports, etc.) and various other components and sub-systems.

As understood by those skilled in the art, processors execute software instructions. Software instructions alone are incapable of performing a function. Therefore, in the present disclosure, any reference to a function performed by software instructions, or to software instructions performing a function is simply a shorthand means for stating that the function is performed by a processor executing the instructions.

The storage 1304 is a non-transitory computer-readable storage medium suitable for storing instructions executable by the processor 1302, and for storing measurements received from the cross-sectional area tool 300 and the sectional wall tool 400, maps of the wall of the tubing string 104, and other data. The storage 1304 may include volatile storage such as random access memory, non-volatile storage (e.g., a hard drive, an optical storage device (e.g., CD or DVD), FLASH storage, read-only-memory), or combinations thereof.

The storage 1304 includes a threshold monitoring module 1306, a zero adjustment module 1308, a rectification module 1310, a standardization module 1312, and a map generation module 1314. These modules include instructions that when executed cause the processor 1302 to perform the operations disclosed herein. For example, the instructions included in the modules 1306-1314, when executed, may cause the processor 1302 to perform the operations of the method 1200, and other operations disclosed herein.

The threshold monitoring module 1306 includes instructions that the processor 1302 executes to compare the level of the signal generated by the cross-sectional area tool 300 (i.e., the signal generated by the measurement coil 304) to a threshold set at a signal level selected to indicate at least a predetermined amount of material loss in the cross-sectional area of the tubular. The threshold monitoring module 1306 may include additional instructions that process the signal generated by the cross-sectional area tool 300 prior to threshold comparison. For example, instructions that are executed by the processor 1302 to integrate the signal generated by the cross-sectional area tool 300 may be included in the threshold monitoring module 1306.

The zero adjustment module 1308 includes instructions that the processor 1302 executes to determine a zero adjustment value for each signal received from the sectional wall tool (i.e., each signal generated by one of the sensors 402), and to apply the zero adjustment value to remove offset from the corresponding signal.

The rectification module 1310 includes instructions that the processor 1302 executes, after signals received from the sectional wall tool 300 have been zero adjusted, to rectify each of the zero adjusted signals.

The standardization module 1312 includes instructions that the processor 1302 executes, after the zero adjusted signals have been rectified, to standardize the rectified zero adjusted signals.

The map generation module 1314 includes instructions that the processor 1302 executes to generate a map of the wall of the tubing string 104. Different wall thicknesses or degrees of material loss may be illustrated using different colors, shades, or other indicators.

The above discussion is meant to be illustrative of various embodiments of the present invention. Numerous variations and modifications will become apparent to those skilled in the art once the above disclosure is fully appreciated. It is intended that the following claims be interpreted to embrace all such variations and modifications.

What is claimed is:

1. A system for detecting material loss in a tubular, comprising:
   a magnetization coil configured to encircle the tubular and generate a magnetic field that induces magnetic flux in the tubular;
   a measurement coil configured to encircle the tubular and detect changes in the magnetic flux caused by variation in the radial cross-section of the tubular;
   a plurality of flux leakage sensors arranged to radially encircle the tubular, each of the flux leakage sensors configured to detect changes in the magnetic field of an arc section of the tubular; and
   a processor coupled to the measurement coil and the flux leakage sensors, the processor configured to:
      identify a radial cross-sectional area of the tubular as having a loss of material in a wall of the tubular based on a flux signal generated by the measurement coil;
      responsive to identification of the loss of material, determine an amount of voltage offset present in each measurement signal generated by the flux leakage sensors;
      for each measurement signal, produce a zero adjusted signal by adjusting the measurement signal to remove the amount of voltage offset over a length of the tubular for which the loss of material is detected;
      produce an assessment of wall material loss for each arc section of the wall of the tubular based on the zero adjusted signals; and
      generate an image of the wall of the tubular showing the wall material loss for each arc section.

2. The system of claim 1, wherein the processor is configured to identify the radial cross-sectional area of the tubular as having a loss of material by detecting a change in magnetic flux caused by a change in the radial cross-sectional area of the tubular caused by loss of material in the wall of the tubular.

3. The system of claim 1, wherein the processor is configured to, for each measurement signal, set the amount of voltage offset to be a value of the measurement signal at a predetermined time prior to identification of loss of material in the wall of the tubular.

4. The system of claim 3, wherein the processor is configured to compute the amount of voltage offset for each measurement signal as an average of a plurality of values of the measurement signal about the predetermined time.

5. The system of claim 1, wherein the processor is configured to, for each measurement signal, subtract the amount voltage offset from each sample of the measurement signal over the length of the tubular for which loss of material is detected.

6. The system of claim 1, wherein the processor is configured to, for each identification of a different radial cross-sectional area of the tubular as having a loss of material in the wall: adjust each of the measurement signals to remove an amount of voltage offset specific to the measurement signal at the different radial cross-sectional area.

7. The system of claim 1, wherein the processor is configured to:
   rectify the zero adjusted signal by inverting negative portions of the zero adjusted signal to produce a rectified signal; and
   standardize the rectified signal to compensate for over-emphasis in the measurement signal at a beginning and end of an area of material loss.

8. A method for detecting material loss in a tubular, comprising:
   identifying a radial cross-sectional area of the tubular as having a loss of material in a wall of the tubular;
   responsive to the identifying, determining an amount of voltage offset present in each of a plurality of measurement signals, wherein each of the measurement signals provides measurement information for an arc section of the wall of the tubular;
   for each of the measurement signals, producing a zero adjusted signal by adjusting the measurement signal to remove the amount of voltage offset over a length of the tubular for which the identifying recognizes the loss of material;
   producing an assessment of wall material loss for each arc section of the wall of the tubular based on the zero adjusted signals; and
   generating an image of the wall of the tubular showing the wall material loss for each arc section.

9. The method of claim 8, wherein the identifying comprises detecting a change in magnetic flux caused by a change in the radial cross-sectional area of the tubular caused by loss of material in the wall of the tubular.

10. The method of claim 8, wherein the determining comprises, for each of the measurement signals, setting the amount of voltage offset to be a value of the measurement signal at a predetermined time prior to identification of loss of material in the wall of the tubular.

11. The method of claim 10, wherein setting the amount of voltage offset comprises averaging a plurality of values of the measurement signal about the predetermined time.

12. The method of claim 8, wherein the adjusting comprises, for each of the measurement signals, subtracting the amount of voltage offset from each sample of the measurement signal over the length of the tubular for which the identifying detects the loss of material.

13. The method of claim 8, further comprising, for each identification of a different radial cross-sectional area of the tubular as having a loss of material in the wall of the tubular, adjusting each of the measurement signals to remove an amount of voltage offset specific to the measurement signal at the different radial cross-sectional area.

14. The method of claim 8, further comprising, for each of the zero adjusted signals:
   rectifying the zero adjusted signal by inverting negative portions of the zero adjusted signal to produce a rectified signal; and
   standardizing the rectified signal to compensate for over-emphasis in the measurement signal at a beginning and end of an area of material loss.

15. A non-transitory computer-readable medium encoded with instructions that when executed cause a processor to:

identify a radial cross-sectional area of the tubular as having a loss of material in a wall of the tubular;

responsive to identification of loss of wall material in a radial cross-sectional area, determine an amount of voltage offset present in each of a plurality of measurement signals, wherein each of the measurement signals provides measurement information for an arc section of the wall of the tubular;

produce, from each of the measurement signals, a zero adjusted signal by adjusting the measurement signal to remove the amount of voltage offset over a length of the tubular for which the loss of material is detected;

produce an assessment of wall material loss for each arc section of the wall of the tubular based on the zero adjusted signals;

generate an image of the wall of the tubular showing the wall material loss for each arc section.

16. The computer-readable medium of claim 15 encoded with instructions that when executed cause the processor to identify the radial cross-sectional area of the tubular as having a loss of material by detecting a change in magnetic flux caused by a change in the radial cross-sectional area of the tubular caused by loss of material in the wall of the tubular.

17. The computer-readable medium of claim 15 encoded with instructions that when executed cause the processor to, for each measurement signal, set the amount of voltage offset to be a value of the measurement signal at a predetermined time prior to identification of loss of material in the wall of the tubular.

18. The computer-readable medium of claim 17 encoded with instructions that when executed cause the processor to compute the amount of voltage offset for each measurement signal as an average of a plurality of values of the measurement signal about the predetermined time.

19. The computer-readable medium of claim 15 encoded with instructions that when executed cause the processor to, for each measurement signal, subtract the amount voltage offset from each sample of the measurement signal over the length of the tubular for which loss of material is detected.

20. The computer-readable medium of claim 15 encoded with instructions that when executed cause the processor to, for each identification of a different radial cross-sectional area of the tubular as having a loss of material in the wall: adjust each of the measurement signals to remove an amount of voltage offset specific to the measurement signal at the different radial cross-sectional area.

21. The computer-readable medium of claim 15 encoded with instructions that when executed cause the processor to:
rectify the zero adjusted signal by inverting negative portions of the zero adjusted signal to produce a rectified signal; and
standardize the rectified signal to compensate for over-emphasis in the measurement signal at a beginning and end of an area of material loss.

* * * * *